United States Patent

Harris, Jr.

Patent Number: 5,514,373
Date of Patent: May 7, 1996

[54] TOPICAL PREPARATION

[76] Inventor: Roosevelt D. Harris, Jr., 6325 Beecher Dr., Charlotte, N.C. 28215

[21] Appl. No.: 886,711

[22] Filed: May 22, 1992

[51] Int. Cl.$^6$ ............................ A61K 38/48; A61K 38/43
[52] U.S. Cl. ......................... 424/94.65; 424/94.1
[58] Field of Search .................. 424/94.65, 94.1

[56] References Cited

U.S. PATENT DOCUMENTS 4,387,094  6/1983  Bagros ..................................... 424/195

OTHER PUBLICATIONS

The Merck Index, 9th Ed, Merck & Co., Inc., Rahway, N.J., 1976, pp. 909–910.

Primary Examiner—Jerome D. Goldberg
Attorney, Agent, or Firm—Timothy R. Kroboth

[57] ABSTRACT

A topical preparation including papain and protease, is provided. Glycerine is present in a major amount, by weight. The preparation promotes healing and the relief of pain.

1 Claim, No Drawings

TOPICAL PREPARATION

FIELD OF THE INVENTION

The invention comprises a medication and more particularly a topical the relief of pain associated with inflamed muscle and joints (including the swelling associated with inflamed joints).

DESCRIPTION OF THE PRIOR ART

Many preparations are available in the prior art for the relief of abnormal body conditions. Some of these materials acted through the relief of pain. Others were designed to prevent infections. Still others acted through a wide variety of mechanisms but all were limited to a defined range of conditions. By contrast, the above described invention provides a material applicable to a wide range of ailments in that it acts to promote the relief of pain associated with inflamed muscles a joints as a result of rheumatoid arthritis, bursitis and osteoarthritis.

SUMMARY OF THE INVENTION

The invention comprises a preparation for a topical application that promotes the relief of pain. More particularly, the preparation comprises a mixture of water (2.86%), papain (0.12%) NaCl (0.28%), glycerine (96.7%), and protease (0.04%). In use, the preparation is applied liberally to the area to be treated. This material has been found to provide relief for a wide variety of conditions which result in pain. As with many medications the exact mechanism responsible for the beneficial results are not well understood at this time. However, normal cell growth is a generic process that is common to the treatment of many abnormal body conditions.

DESCRIPTION OF THE INVENTION

The preparation comprising the invention is a solution which includes selected combinations of water, papain, NaCl, glycerine and protease and shown in Table 1. While these ingredients have found wide use individually and in combination with other ingredients, no preparation similar to the invention has been found per the medical literature. Additionally, the preparation comprising the invention has been found to be a medically useful preparation when used as herein described. In preparing the preparation comprising the invention, the ingredients are prepared in the desired amount and mixed to produce the final preparation. The ingredients may be purchased from commercial suppliers of such products. Thus they are easily obtained and mixed without any unusual techniques being necessary. Specifically, in the preferred embodiment the major ingredient by weight is glycerine with each of the other aforedescribed ingredients in amounts as shown in Table 1.

However, the various ingredients do synergistically interact when topically applied to the human body to generate desirable medical results. More specifically, the preparation has been found to be beneficial in treating the following conditions:

1) bursitis;
2) rheumatoid arthritis;
3) inflamed muscles and joints; and
4) sore muscles due to excessive exercise.

All of the above conditions are believed to involve body conditions in which various body structures include cells having abnormal chemical conditions. These abnormalities may result from physical injury, aging or other causes. However, they all include the possibility that topically applied materials which are capable of promoting relief of pain and swelling of muscles and joints can be of great value when applied as an agent. There is a demonstrated synergistic combination of the ingredients. Additionally, some of the ingredients have medical uses outside of the disclosed combination. Similarly, glycerine and its compounds are found in many medical products.

TABLE I

| Ingredients of Preparation | | |
|---|---|---|
| | Weight | Percent |
| Glycerin | 480 g | 96.70 |
| Protease | .2 g | .04 |
| Papain-Papinase | .6 g | .12 |
| NaCl | 1.4 g | .28 |
| $H^2O$ | 14.2 g | 2.86 |
| Total: | 496.4 g | 100.00% |

With the exception of glycerine, all of the ingredients are combined with $H^2O$ until the NaCl is dissolved (by shaking the solution When the salt is dissolved, pour it in glycerin and cap it. Shake the solution. The mixing is a slow process (at room temperature, the capped solution will take two weeks to complete the mixing). The process can be expedited by heating the glycerine to about or 75 degrees F. before introducing the other ingredients. This should cut the mixing time in half.

I claim:

1. A topical preparation consisting essentially of

| papain | 0.2 to 2 wt. % |
|---|---|
| protease | 0.2 to 2 wt. % |
| NaCl | 0.2 to 2 wt. % |
| water | 0.2 to 2 wt. %, and |
| glycerine | major amount, by weight. |

* * * * *